(12) United States Patent
Klein et al.

(10) Patent No.: US 7,098,374 B2
(45) Date of Patent: Aug. 29, 2006

(54) HUMAN DISEASE MODELING USING SOMATIC GENE TRANSFER

(75) Inventors: Ronald Klein, Gainesville, FL (US); Edwin Meyer, Gainesville, FL (US); Nicholas Muzyczka, Gainesville, FL (US); Mike King, Gainesville, FL (US); Craig Meyers, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/780,041

(22) Filed: Feb. 9, 2001

(65) Prior Publication Data

US 2002/0111321 A1 Aug. 15, 2002

(51) Int. Cl.
*A01K 67/00* (2006.01)
*A01K 67/033* (2006.01)

(52) U.S. Cl. ............................................ 800/9; 800/12

(58) Field of Classification Search .............. 435/320.1, 435/455; 800/3, 13, 14, 18, 21, 8, 9, 12; 424/93.1, 93.2, 93.6; 514/44
See application file for complete search history.

(56) References Cited

U.S. PATENT DOCUMENTS

| 5,720,720 A | 2/1998 | Laske et al. |
| 6,027,931 A | 2/2000 | Natsoulis et al. |
| 6,071,889 A | 6/2000 | Weiss et al. |

FOREIGN PATENT DOCUMENTS

WO   WO 99/61066   12/1999

OTHER PUBLICATIONS

Hammer et al. (1990) Spontaneous inflammatory disease in transgenic rats expressing HLA-B27 and human beta-2 microglobulin. Cell 63: 1099-1112.*
Houdebine, LM (1994) Production of pharmaceutical proteins from transgenic animals. J. Biotechnology 34: 269-287.*
Kappel et al. (1992) Regulating gene expression in transgenic animals. Curr. Opinion in Biotechnology 3: 548-553.*
Mullins et al. (1990) Fulminant hypertension in transgenic rats harbouring the mouse Ren-2 gene. Nature 344: 541-544.*
Mullins et al. (1989) Expression of the DBA/2J Ren-2 gene in the adrenal gland of transgenic mice. EMBO J. 8(13): 4065-4072.*
Sigmund (2000) Viewpoint: Are studies in genetically altered mice out of control? Arterioscler. Thromb. Vasc. Biol. 20: 1425-1429.*
Strojek and Wagner (1988) The use of transgenic animal techniques for livestock improvement. Genetic Engineering: Principles and Methods 10: 221-246.*
Taurog et al. (1988) HLA-B27 in inbred and non-inbred transgenic mice. J. Immunol. 141(11): 4020-4023.*
Wall, RJ (1996) Transgenic livestock: Progress and prospects for the future. Theriogenology 45: 57-68.*
Gotz et al. (2001) Tau filament formation in transgenic mice expressing P301L Tau. J. Biol. Chem. 276(1): 529-534.*
Lewis et al. (2000) Neurofibrillary tangles, amyotrophy and progressive motor disturbance in mice expressing mutant (P301L) tau proteint. Nature Genetics 25: 402-405.*
Klein, Ronald, L. et al., "Neuron-Specific Transduction in the Rat Septohippocampal or Nigrostiatal Pathway by Recombinant Adeno-associated Virus Vectors", *Experimental Neurology*, 1998, 183-194: 150, Academic Press.
Klein, Ronald, L. et al., "Long-Term Action of Vector-Derived Nerve Growth Factor or Brain-Derived Neurotrophic Factor on Choline Acetyltransferase and TRK Receptor Levels in the Adult Casal Forebrain", *Neuroscience*, 1999, 815-821: 90-3, Elsevier Science Ltd., Great Britain.
Klein, Ronald, L. et al., "Prevention of 6-hydroxydopamine-induced Rotational Behavior by BDNF Somatic Gene Transfer", *Brain Research*, 1999, 314-320, Elsevier Science.
Price, Donald, L. et al., "Genetic Neurodegenerative Diseases: The Human Illness and Transgenic Models", *Science*, 1998, 1079-1083: 282.
Hsiao, Karen, et al., "Correlative Memory Deficits, Aβ Elevation, and Amyloid Plaques in Transgenic Mice", *Science*, 1996, 99-10: 274.
Duff, Karen, et al., "Increased Amyloid-β42(43) in Brains of Mice Expressing Mutant Presenilin 1", *Nature*, 1996, 710-713: 383.
Parimala, Nacharaju, et al., "Accelerated Filament Formation From Tau Protein With Specific FTDP-17 Missence Mutation", *FEBS Letters*, 1999, 195-199:447 , Federation of European Biomedical Societies.
Polymeropoulos, Mihael, et al., "Mutation in the α-Synuclein Gene Identified in Families with Parkinson's Disease", *Science*, 1997, 2045-2047: 276.
Kruger, Rejko, et al., "Ala30Pro Mutation in the Gene Encoding α-synuclein in Parkinson's Disease", *Nature Gentics*, 1998, 106-108:18.
Abeliovich, Asa, et al., "Mice Lacking α-Synuclein Display Functional Deficits in the Nigrostriatal Dopamine System", *Neuron*, 2000, 239-252: 25, Cell Press.
Dickinson, Dennis, W., et al., "Tau and Synuclein and Their Role in Neuropathology", *Brain Pathaology*, 1999, 657-661: 9.

(Continued)

*Primary Examiner*—Anne-Marie Falk
(74) *Attorney, Agent, or Firm*—Timothy H. Van Dyke; Beusse Wolter Sanks Mora & Maire, P.A.

(57) ABSTRACT

This invention provides a system for modeling neurodegenerative and other diseases through somatic gene transfer. In addition, methods of multiple gene transfer, disease analysis and drug testing are provided for.

4 Claims, 7 Drawing Sheets

OTHER PUBLICATIONS

Buxbaum, Joseph, D., et al., "Expression of APP in the Brains of Transgenic Mice Containing the Entire Human A*PP* Gene", *Boichemical and Biophysical Research Communications*, 1993, 639-645, 197:2, Academic Press, Inc.

Higgins, L.S., et al., "Transgenic Mouse Brain Histopathology Resembles Early Alzheimer's Disease", *Ann Neurol*, 1994, 598-607: 35, American Neurological Association.

Laferla, Frank, M., et al., "The Alzheimer's Aβ Peptide Induces Neurodegenration and Apoptotic Cell Death in Trasgenic Mice", *Nature Genetics*, 1995, 21-30: 9.

Lamb, Bruce, T., et al., "Introduction and Expression of the 400 Kilobase *Precursor Amyloid Protein* Gene in Transgenic Mice", *Nature Genetics*, 1993, 22-30: 5.

Moran, Paula, M., et al., "Age-related Learning Deficits in Transgenic Mice Expressing the 751-Amino Acid Isoform of Human β-amyloid Precursor Protein", *Proc. Natl. Acad. Sci.*, 1995, 5341-5345: 92.

Hsiao, Karen, K. et al., "Age-related CNS Disorder and Early Death in Transgenic FVB/N Mice Overexpressing Alzheimer Amyloid Precursor Proteins", *Neuron*, 1995, 1203-1218: 15, Cell Press.

Nalbantoglu, J., et al, "Impaired Learning and LTP in Mice Expressing the Carboxy Terminus of the Alzheimer Amyloid Precursor Protein", *Nature*, 1997, 500-505: 387.

Lamb, Bruce, T. et al., "Altered Metabolism of Familial Alzheimer's Disease-linked Amyloid Precursor Protein Variants in Yeast Artificial Chromosone Transgenic Mice", *Human Molecular Genetics*, 1997, 1535-1541, 6: 9, Oxford University Press.

Kammesheidt, Anja, et al, "Depositon of β/ A4 Immunoreactivity and Neuronal Pathology in Transgenic Mice Expressing the Carboxyl-Terminal Fragment of the Alzheimer Amyloid Precursor in the Brain", *Proc. Natl. Acad. Sci.*, 1992, 10857-10861: 89, USA.

Peel, Alyson, L. and Klein, Ronald, L., "Adeno-associated Virus Vectors: Activity and Applications in the CNS", *Journal of Neuroscience Methods*, 2000, 95-104:98, Elsevier Science.

Klein, Ronald, L. et al., "NGF Gene Transfer to Intrinsic Basal Forebrain Neurons Increases Cholinergic Cell Size and Protects From Age-Related, Spatial Memory Deficits in Middle-Aged Rats", *Brain Research*, 2000, 144-151: 875, Elsevier Science.

Klein, Ronald, L. et al., Adeno-Associated Virus Vector Mediated Gene Transfer to Somatic Cells in the Central Nervous System, *Advances in Virus Res.* Edited by K. Maramorosch, F.A. Murphy, A.J. Shatkin, J.C. Glorioso, 2000, 507-528: 55, Academic Press, SanDiego.

\* cited by examiner pCB-APP pCB-PS1 pCB-tau pCB-tau301 pCB-αsyn pCB-αsyn30 pCB-αsyn53

HUMAN DISEASE MODELING USING SOMATIC GENE TRANSFER

"This invention was made with government support under National Institutes of Health grant number AR 1382-42A1. The government has certain fights in the invention."

FIELD OF THE INVENTION

This invention provides a system for modeling neurodegenerative and other diseases through somatic gene transfer. In addition, methods of multiple gene transfer, disease analysis and drug testing are provided for.

BACKGROUND TO THE INVENTION

Numerous methods of gene transfer are known in the art, and are not reviewed in any great detail here. Suffice it to say that in general, methods of gene transfer in vitro are well known and have been practiced for several decades. Methods of in vivo gene transfer are much more recent, but have been successfully applied in such contexts as gene therapy efforts to overcome genetic disorders, and in disease modeling efforts, such as the production of germ-line transgenic animal models, such as gene knockout mice or transgenic mice and other animals expressing heterologous genes.

In general, the known methods of in vivo gene transfer involve the knockout of single genes present in the genome of an animal model, or the inclusion in the germ-line of a specific transgene in the genome of an animal model. The limitations to such methods include the possibility of inducing terminal illnesses in the animal models, such that either non-viable fetuses are produced, or limited life-span animals are produced. In addition, the effects of multiple gene knockouts or transgenes are extremely difficult to simulate in such systems, due to the complex temporal, gene regulatory and interaction effects in such systems. Furthermore, the germ-line transgenic models currently available tend to provide data on a very slow time scale, and such efforts as drug modeling and disease analysis are delayed by the time-scale of transgenic animal maturation. Accordingly, there remains a need in the art for techniques which address and overcome these limitations. This invention is directed to resolving many, if not all, of these limitations in the art.

BRIEF DESCRIPTION OF THE DRAWINGS

FIG. 3, panels 3A to 3F, show the expression of somatically introduced trausgenic tau. FIG. 3C shows robust levels of neurons expressing tan in the septum and diagonal band at low magnification. There is a lack of staining in the non-transduced tissue (the right edge of FIG. 3C). FIG. 3D shows higher magnification of the transduced cells showing somatodendritic accumulation of tau immunostaining that resemble flame-shaped neurofibrillary tangles. Higher magnification of tau accumulation in a medial septal neuron is seen in the FIG. 3D inset. FIG. 3 further shows the expression of P301L tau, and that expression resulted in tau aggregation in neuronal cell bodies and dendrites of the adult rat basal forebrain.

SUMMARY OF THE INVENTION

Figure 1:
FIG. 1 shows examples of DNA constructs utilized according to the present invention. The figure shows schematic representations of expression cassettes which are packaged into recombinant adeno-associated virus (AAV) vectors; abbreviations: TR, AAV terminal repeats; PrCBA, cytomegalovirus/chicken beta-actin hybrid promoter; IRES, internal ribosome entry sequence which allows for bicistronic expression of two transgenes; gfp, green fluorescent protein; pA, poly adenylation sequence. Human DNA sequences to model neurodegenerative diseases: APP, amyloid precursor protein mutant form linked to Alzheimer's disease; presenilin 1 mutant form linked to Alzheimer's disease; tau wild type and mutant form linked to fronto-temporal dementia with Parkinsonism linked to chromosome 17; alpha-synuclein wild type and mutant forms linked to Parkinson's disease.
Figure 1:
Figure 1:
Figure 1:
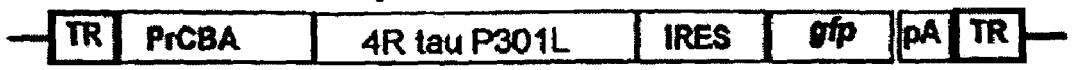
Figure 1:
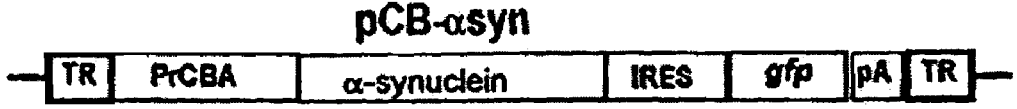
Figure 1:
Figure 1:
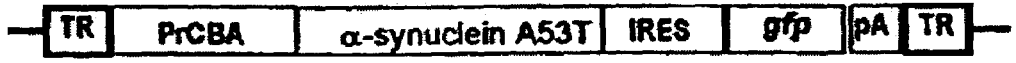

This invention provides a system for modeling neurodegenerative and other diseases through somatic gene transfer. In addition, methods of multiple gene transfer, disease analysis and drug testing are provided for. Advantages of the somatic gene transfer (SGT) methodology of this invention include:

a. The ability to more precisely control the location to which the genes are transferred (i.e. spatial control of gene expression);

b. The ability to more precisely analyze the temporal effects of transferred genes at specific times in the development of otherwise normal organisms (i.e. temporal control of gene expression);

c. The ability to evaluate the effects of expression of combinations of multiple transgenes, which in a germline transgenic animal would be difficult if not impossible to achieve due to diseases which might prevent the animal model from maturing to the age-appropriate state for modeling onset of a particular, complex human disease, such as Alzheimer's.

d. Reduced cost.

e. Faster method for analyzing multiple genes which contribute to complex, multifactorial neurodegenerative diseases.

f. The models can be used for drug testing against specific neurodegenerative diseases as well as for studying the pathologies themselves.

g. The methodology provides a means to supplement existing germline transgenic models with additional somatically provided gene products to modulate the transgenic model.

h. Additionally, another possibly unique aspect of this technology is its emphasis on the creation of a disease condition in an otherwise healthy animal, as opposed to, say, gene therapy techniques developed to treat disease conditions, or germ-line based disease models in which the animal model is diseased (if only nacently) from the outset.

Accordingly, objects of this invention include provision of a system which meets any or all of the foregoing criteria. In specific embodiments of this invention, such diseases as Alzheimer's Disease (AD), Parkinson's Disease (PD), and Huntington's Disease (HD) are effectively modeled through somatic gene transfer, as opposed to known methods of germline transgenesis. This patent disclosure demonstrates the present inventors' ability to produce brain aggregates through somatic gene transfer of a mutant form of human tau (P301L), known to be associated with "fronto-temporal dementia with Parkinson's linked to chromosome 17 (FTDP-17)", or through somatic gene transfer of mutant α-synuclein (A30P), known to be associated with PD. This patent disclosure also discloses success in somatic expression of a mutant amyloid precursor protein (APP), and of a mutant presenilin-1 (PS1), mutant forms of each of which are known to be associated with AD.

DETAILED DISCLOSURE OF THE PREFERRED EMBODIMENTS

This invention provides a system for modeling neurodegenerative and other diseases through somatic gene transfer. In addition, methods of multiple gene transfer, disease analysis and drug testing are provided for. Naturally, variations on this theme, as well as other aspects of the invention and equivalents thereof are to be considered as part of the present patent disclosure.

As opposed to methods of germ-line modification of animals to produce models of various neurodegenerative and other diseases, or methods of transferring genes to achieve therapeutic results, this patent disclosure is directed to methodology wherein a disease state analog is produced in an animal model via somatic gene transfer.

As used herein, the term "somatic gene transfer" or "SGT" is intended to mean the process whereby a gene not normally present in an organism is transferred into that organism in a manner that does not implicate the modification of the germ-line of the recipient organism. In other words, if the recipient organism were to produce progeny, in general, the process of SGT would not result in inheritance of the transferred genes to the progeny. This is not to say that it is impossible for genes transferred to an organism by SGT to be incorporated into the germ line of the recipient organism and thence transferred to progeny. Such events as viral induced gene incorporation, transposon mediated gene integration and the like, could conceivably result in the incorporation of genes transferred by SGT into a recipient organism's germ line. However, it should be understood that this is not a principal purpose of conducting SGT. SGT may, however, be practiced according to the present invention in a recipient which already has a modified germ line. For example, a mouse having a particular gene knockout in its germ plasm may, through SGT, be induced to express one or more other genes. In this manner, it is possible to analyze the effects and interplay of the given gene knockout with the genes transferred by SGT.

SGT is achieved according to the present invention by appropriately cloning genes, known or hereafter discovered, to appropriate gene regulatory signals, such that upon introduction into an organism, the relevant genes introduced by SGT are transcribed and translated appropriately, to exert a biological effect. Those skilled in the art are well familiar with appropriate gene expression promoters, terminators, enhancers, vectors and the like, and this patent disclosure therefore does not review in great detail those methodologies and compositions with which those skilled in the are well familiar.

In one preferred embodiment according to the present invention, SGT is achieved using appropriately constructed viral vectors. Viral vectors that may be used according to this invention include, but are not limited to, lentivirus vectors, herpes virus vectors, adenovirus vectors, retroviral vectors, and equivalents thereof. One preferred viral vector system for this purpose includes the use of recombinant adeno-associated viral (AAV) vectors. AAV's are efficient, their infection is relatively long-lived and is generally non-toxic, unless a toxic transgene is recombined therein. AAV is a small, helper-dependent parvovirus consisting of a single strand 4.7 kb DNA genome surrounded by a simple, non-enveloped icosahedral protein coat. Approximately 85% of the adult human population is seropositive for AAV. However, no pathology as been associated with AAV infection. Adenovirus or herpesvirus is generally required as a helper virus to establish productive infection by AAV. In the absence of helper virus, the AAV genome also amplifies in response to toxic challenge, e.g. UV irradiation, hydroxyurea exposure, and the like. In the absence of either toxic challenge or helper virus, wild-type AAV integrates into human chromosome 19 site-specifically as a function of AAV Rep proteins that mediate the formation of an AAV-chromosome complex at the chromosomal integration site. Up to 96% of the viral genome may be removed, leaving only the two 145 base pair (bp) inverted terminal repeats (ITRs) which are sufficient for packaging and integration of the viral genome. Methods for efficient propagation of recombinant AAV, rAAV, have been developed in the art, including the use of mini-adenoviral genome plasmids, plasmids encoding AAV packaging functions and adenovirus helper functions in single plasmids. Furthermore, methods of rAAV isolation have developed to the point where methods for isolation of highly purified rAAV are a relatively straightforward and rapid undertaking. Likewise for methods of titration of rAAV stocks. Use of green fluorescent protein (GFP) a well-characterized 238 amino acid fluorescent protein is frequently used in a bicistronic arrangement in rAAV to trace rAAV-mediated transgene expression. Promoters for selective and specific expression of rAAV mediated gene transfer have also been identified.

Methods of making and using rAAV and delivery of rAAV to various cells in vivo are disclosed in U.S. Pat. Nos. 5,720,720; 6,027,931; 6,071,889; WO 99/61066; all of which are hereby incorporated by reference for this purpose.

With regard to methods for the successful, localized, long-term and non-toxic transgene expression in the nervous system through SGT using adeno-associated virus (AAV) and selected promoters, reference is made to Klein et al, 1998, Experimental Neurology 150:183–194, "Neuron-Specific Transduction in the Rat Septohippocampal or Nigrostriatal Pathway by Recombinant Adeno-associated Virus Vectors".

With respect to a method of gene therapy using recombinant AAV with significant persistence through stable expression of the neurotrophic factors NGF or BDNF, and resultant neurochemically quantifiable therapeutic effects, reference is made to Klein et al, Neuroscience 90:815–821, "Long-term Actions of Vector-derived Nerve Growth Factor or Brain-derived Neurotrophic Factor on Choline Acetyltransferase and Trk Receptor Levels in the Adult Rat Basal Forebrain."

With regard to achievement of quantifiable behavioral effects through somatic transgene expression in the nervous system through AAV vectored expression of BDNF, reference is made to Klein et al, 1999, Brain Research 847: 314–320, "Prevention of 6-hydroxydopamine-induced Rotational Behavior by BDNF Somatic Gene Transfer."

With respect to a review of the state of the art of germline transgenic mouse models for neurodegenerative diseases, including a large number of references in the field of germline transgenic mouse modeling of neurodegenerative diseases, reference is made to Price et al, 1998, Science 282:1079–1083, "Genetic Neurodegenerative Diseases: The Human Illness and Transgenic Models."

With regard to a review of the state of the art of germline transgenic mouse models for neurodegenerative diseases, including a large number of references in the field of germline transgenic mouse modeling of neurodegenerative diseases, reference is made to PCT Publication WO99/61066, Published Dec. 2, 1999, Avigen, Inc., based on Prior U.S. Applications filed May 27, 1998 and May 18, 1999, "Convection-Enhanced Delivery of AAV Vectors". However, the review does not substantively address somatic cell transgenesis methodology.

As with the WO99/61066 publication discussed above, reference is made to U.S. Pat. No. 5,720,720, "Convection-Enhanced Drug Delivery", for its disclosure of methods relating to the delivery of various compounds, including viruses, to the CNS via CED.

With respect to administration of genes to neural precursor cells induced to divide through contact with growth factors to facilitate incorporation of the genetic material into the cell progeny, reference is made to U.S. Pat. No. 6,071,889, "In Vivo Genetic Modification of Growth Factor-Responsive Neural Precursor Cells." AAV mediated gene delivery is mentioned, although the method appears to be limited to the ex vivo administration of nucleic acids and growth factors to neuronal cells, and the thus treated cells are then administered to the living organism.

With regard to genes known in the art to which reference is made herein, amyloid precursor protein, APP, was described by Hisao et al, 1996, "Correlative memory deficits, AB elevation, and amyloid plaques in transgenic mice," Science 274:99–102. Presenilin-1, PS-1, was described by Duff et al, "Increased amyloid-beta 42(43) in brains of mice expressing mutant presenilin 1," Nature 1996, 383(6602): 710–713. Tau was described by Nacharaju et al 1999, "Accelerated filament formation from tau protein with specific FTDP-17 missense mutations," FEBS Letters 447: 195–199. Alpha-synuclein was described by Polymeropoulos et al, 1997 "Mutation in the alpha-synuclein gene identified in families with Parkinson's disease," Science 276:2045–2047; and by Kruger et al., "Ala30Pro mutation in the gene encoding alpha-synuclein in Parkinson's disease," Nat. Genet. 18(1998):106–108. All of these references are hereby incorporated by reference for their teachings of these genes.

Turning now to specific applications of the present invention, wherein SGT is used to induce specific disease states is an appropriate animal model, examples are provided herein of success achieved by the instant inventors in the particularly challenging area of neurodegenerative disease modeling. Those skilled in the art will appreciate that the present invention should not be restricted to the specifics of the examples provided herein, because the operative principles for achieving success in the particularly challenging area of neurodegenerative diseases also apply in less challenging areas of human disease modeling, not requiring delivery of genes to the central nervous system (CNS). In addition, those skilled in the art will appreciate that the present invention is particularly useful in modeling diseases of the CNS, because of the refined control that the present methodology provides in terms of the ability to specifically target selected CNS tissues of interest. In addition, advantages of this invention include:

(a) The ability to more precisely control the location to which the genes are transferred (i.e. spatial control of gene expression);
(b) The ability to more precisely analyze the temporal effects of transferred genes at specific times in the development of otherwise normal organisms (i.e. temporal control of gene expression);
(c) The ability to evaluate the effects of expression of combinations of multiple transgenes, which in a germline transgenic animal would be difficult if not impossible to achieve due to diseases which might prevent the animal model from maturing to the age-appropriate state for modeling onset of a particular, complex human disease, such as Alzheimer's.
(d) Reduced cost.
(e) Faster method for analyzing multiple genes which contribute to complex, multifactorial neurodegenerative diseases.
(f) The models can be used for drug testing against specific neurodegenerative diseases as well as for studying the pathologies themselves.
(g) The methodology provides a means to supplement existing germline transgenic models with additional somatically provided gene products to modulate the transgenic model.
(h) Additionally, another possibly unique aspect of this technology is its emphasis on the creation of a disease condition in an otherwise healthy animal, as opposed to, say, gene therapy techniques developed to treat disease conditions, or germ-line based disease models in which the animal model is diseased (if only nacently) from the outset.

Accordingly, objects of this invention include provision of a system which meets any or all of the foregoing criteria. In specific embodiments of this invention, such diseases as Alzheimer's Disease (AD), Parkinson's Disease (PD), and Huntington's Disease (HD) are effectively modeled through somatic gene transfer, as opposed to known methods of germline transgenesis. This patent disclosure demonstrates the present inventors' ability to produce brain aggregates through somatic gene transfer of a mutant form of human tau (P301L), known to be associated with "fronto-temporal dementia with Parkinson's linked to chromosome 17 (FTDP-17)", mutant α-synuclein (A30P), known to be associated with PD. This patent disclosure also discloses success in somatic expression of a mutant amyloid precursor protein (APP), and of a mutant presenilin-1 (PS1), mutant forms of each of which are known to be associated with AD. Other genes of interest with respect to practice of the methods of this invention include, but are not limited to: GAP43, interleukins, especially interleukin-6 (IL-6), gamma-secretase, and combinations thereof. Particularly preferred combinations of genes for transfer to an animal model in accordance with the methodology of this invention include, but are not limited to: APP in combination with presenilin; APP in combination with presenilin plus tau; APP in combination with presenilin plus tau plus IL6; combinations, permutations and variations thereof.

Mutations in the genes for tau and alpha-synuclein can result in abnormal protein deposition, formation of neurofibrillary tangles and Lewy bodies, and death of specific neuron populations. For example, splice site and mis-sense mutations in the tau gene are found in families of neurofibrillary pathology like frontotemporal dementia with Parkinsonism linked to chromosome 17. Transgenic models of neurodegeneration provide functional genomic information about the impact of inherited mutations. Accordingly, somatic cell transgenic models of neurodegeneration are useful for functional genomic studies at particular time points in the lifespan and in particular brain regions. In addition to providing spatio-temporal control of transgene expression, the adeno-associated viral (AAV) vector system enables mixed gene combinations, which are important for complex neurological diseases. Many of these mutant genes are by now well known in the art, having been cloned sequenced and extensively characterized. Accordingly, those skilled in the art, based on the instant disclosure, would be fully enabled to practice the present methods of SGT using such genes known in the art, as well as genes hereafter identified as playing potential roles in development of human neurodegenerative, as well as other human diseases. As a result, the methods disclosed herein provide versatile systems for modeling human diseases, as well as various veterinary diseases, in a rapid, efficient manner, which does not require the delay and complexity of germline disease modeling.

According to the present disclosure, certain specific nucleic acid vector constructs are disclosed by way of exemplary support. Reference is made to FIG. 1 herein, which shows DNA constructs which may be used according to the methods of this invention. Those skilled in the art will appreciate that, based on this disclosure, a wide variety of disease-causing genes, transcriptional promoters, translational regulators, effectors, initiators, cis and trans acting elements, enhancers, marker genes, and the like may be employed according to the methods disclosed herein, without departing from the heart of this invention, namely the induction of disease states in an appropriate animal model through somatic transfer of expressible gene constructs. Those skilled in the art will further appreciate, based on the present disclosure that the methods disclosed herein are also applicable to such models of disease states where a germline modification has been made, and somatic gene transfer is accomplished in the genetic background of an already altered germline in order to elucidate such effects as masking of one allele by another, synergistic effects between different defective alleles, gene knockouts, and the like.

EXAMPLE 1

Induction of Tauopathy in Animal Models

The present inventors have expressed a mutant form of human tau (P301L) using an AAV vector system in the septal nucleus of the basal forebrain and the hippocampus in the adult rat. The vector-derived tau accumulated in cell bodies and dendrites and formed aggregates as observed by co-localization with the reporter gene, green fluorescent protein (GFP), which was bicistronically expressed by the vector (i.e., GFP filled neurons and tau distribution within cell bodies was clustered). The neurofibrillary pathology observed in this model shows abnormal accumulation of tau in neuron cell bodies and dendrites, filaments immunoreactive for hyperphosphyorylated tau, neuritic immunoreactivity for several antibodies that recognized neurofibrillary tangles in Alzheimer's and FTDP-17, and a dramatic induction of reactive astrogliosis. See FIG. 3 provided herewith and the description thereof provided hereinabove. The expression through somatic gene transfer of an aberrant protein, (P301L Tau), found selectively in and known to be associated with Alzheimer's disease, demonstrates that the present invention provides a good model for this a other neurodegenerative diseases.

EXAMPLE 2

SGT as a Method for Supplementing Germline Animal Models

Another utility of the present vector system is to apply genes in trans to existing germline mouse and other animal models, for example, by expressing tau in current models of amyloidosis to introduce tangles.

EXAMPLE 3

Induction of Parkinson's Disease Associated CNS Lesions in Animal Models

A gene linked to autosomal dominant Parkinson's disease, alpha-synuclein, harboring the A30P mutation, was expressed in the rat substantia nigra. Transduced neurons in this area had aggregates rich in alpha-synuclein and axons with large varicosities (5–10 micrometers in diameter) that were not found in control vector samples. Overexpression of alpha-synuclein in the nigrostriatial pathway also elevated rates of amphetamine-stimulated locomotor behavior, which is apparently consistent with reduced locomotor response in alpha-synuclein knockout mice (Abeliovich et al., 2000). Accordingly, it is concluded that the somatic transgenic models disclosed herein are useful for studying mechanisms of neurodegenerative disease pathogenesis as well as gene structure-function relationships of tau and alpha-synuclein.

EXAMPLE 4

Figure 2A:
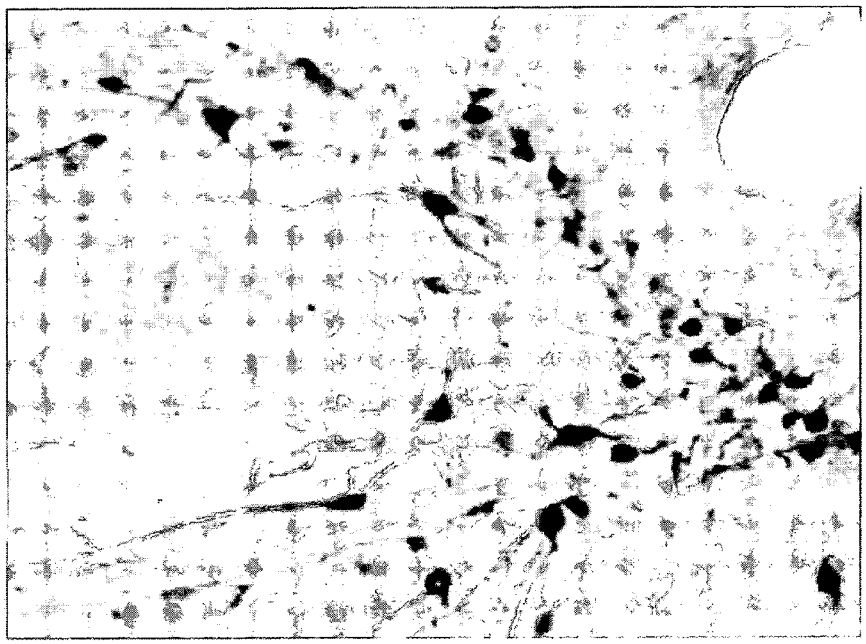
FIG. 2, top panel, shows neurons that are expressing somatically introduced transgenic APP, while the bottom panel shows neurons that are expressing somatically introduced transgenic PS-1 in the hippocampus region.
Figure 2B:
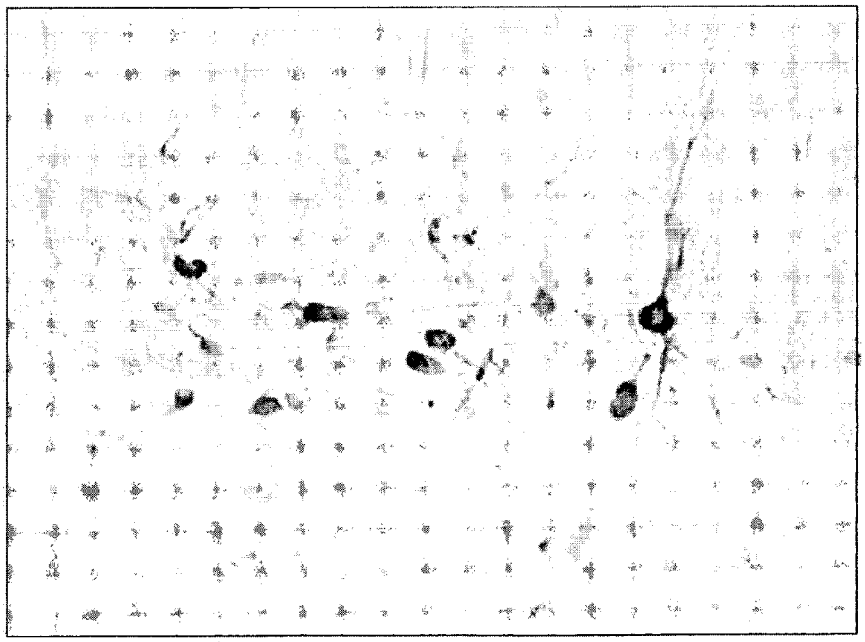

Parkinson's Disease Associated CNS Lesions in Animal Models Using SGT of This Invention Induce Similar Behavioral and Morphologig Lesions to Those Found in Germline Transgenic Animal Models Through practice of the SGT method of this invention, we have found in connection with Parkinson's Disease that alpha synuclein overexpression causes a behavioral change in locomotor activity associated with dopamine transmission. In addition, we have found that cellular processes are essentially identical to those seen in standard germline transgenic animal models (see FIG. 2 provided herein) produced using alpha synuclein expression. See FIG. 4 and the description thereof provided hereinabove.

EXAMPLE 5

Alzheimer's Disease Associated CNS Lesions in Animal Models Using SGT of This Invention Induce Similar Behavioral and Morphologic Lesions to Those Found in Germline Transgenic Animal Models Through practice of the SGT method of this invention, we have found in connection with Alzheimer's Disease that tau overexpression causes intracellular distribution of the protein that is essentially identical to that seen in the only existing germline transgenic animal model in which neurofibrillary tangles associated with the disease are observed. The neuritic damage observed by the present inventors in using the SGT methodology of this invention is similar to that seen in germline transgenic mice overexpressing the gene.

EXAMPLE 6

Alzheimer's Disease Associated CNS Lesions in Animal Models Using SGT of This Invention Induce Similar Behavioral and Morphologic Lesions to Those Found in Germline Transgenic Animal Models Reference is made here to FIGS. 1 and 2 of D. W. Dickson, "Tau and alpha-synuclein and their role in neuropathology, Brain Pathology", 9:65–661 (1991), where tau and synuclein immunohistochemistries are shown, which demonstrate some of the neuropathological processes associated with age-related disease states such as Alzheimer's, Picks, and Parkinson's diseases. It is noted that cells appear to be filled with gene products that appear to be overproduced in such diseases. Notable types of aberrant gene products include tau, amyloid, and synuclein.

Figure 3A:
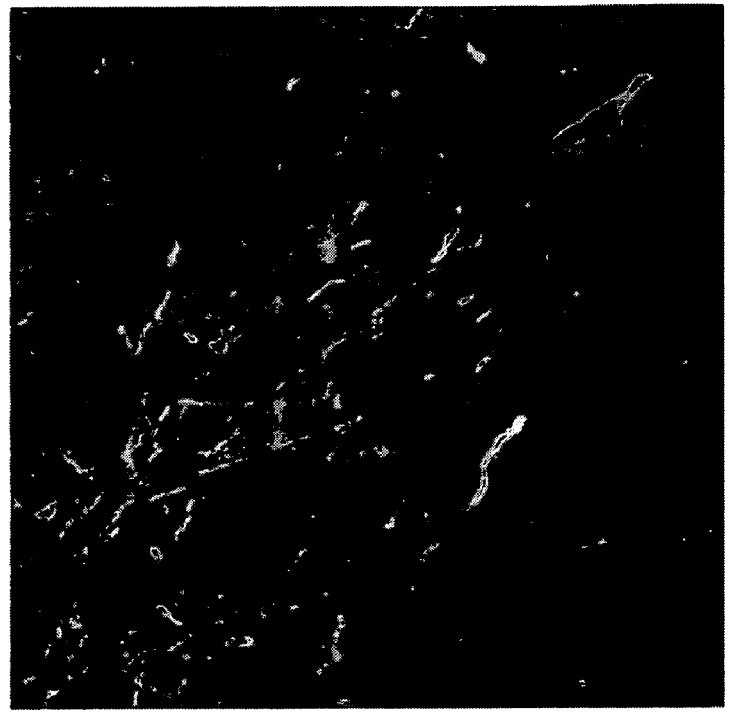
FIGS. 3A and 3B show the hippocampus region, with filamentous structures characteristic of this protein in neurons also being evident. The animals from which tissue was examined for FIGS. 3A and 3B received multiple genes as follows: APP, PS1, IL6 and Tau. (the behavioral modifications induced in these animals, as compared to controls, is shown in FIG. 5). Examples were found of an extracellular tau-immunoreactive deposit, about the size of a neuronal soma, in the toroidal shape reminiscent of the "ghost tangle" of Alzheimer's disease. This figure further shows that human tau gene transfer (single gene) through injection of the human four microtubale binding domain repeat P30 1L tau vector ($1\times10^{10}$ particles in 2 µl injected 3 months earlier) led to robust expression of human tau in septal neurons of the basal forebrain.
Figure 3B:
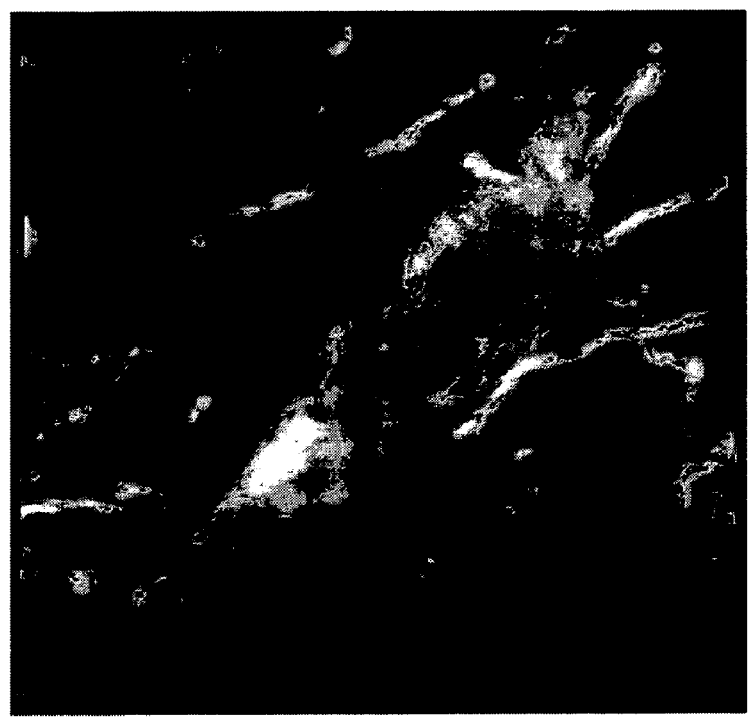
Figure 3C:
FIG. 3C shows low-magnification of the injected area, near the midline in the septal nucleus and diagonal band. Tau immunoreactivity was produced along the injection, mainly on the left side of FIG. 3C. The right edge of FIG. 3C shows surrounding, non-transduced tissue. The monoclonal antibody was specific for human tau and did not produce endogenous staining in the rat tissue.
Figure 3D:
FIG. 3D is a confocal micrograph showing higher magnification of a neuron stained with the tan antibody where immunoreactive filaments with morphology reminiscent of flame-shaped neurofibrillary tangles are observed. This figure demonstrates that somatic gene transfer can increase tan expression and damage neurons in a manner seen in a variety of neurological disorders which encompass pathological deposits of tau, such as Alzheimer's disease, fronto-temporal dementia with Parkinsonism linked to chromosome 17, amyotropic lateral sclerosis, Down's syndrome, Hallervorden-Spatz disease, Jalcob-Creutzfeldt disease, multiple system atrophy, Pick's disease, and others.
Figure 3E:
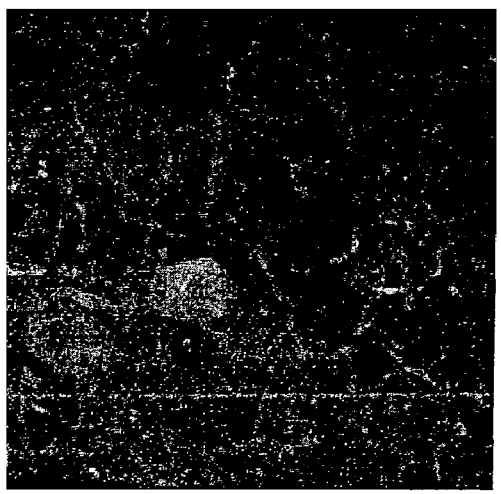
FIGS. 3E and 3F show confocal imaging of fluorescently labeled tau (red) and bicistronic GFP native fluorescence, 2 months after tau vector gene transfer into the septum. Tau expression was somatodendritic as well as axonal, and punctate in places. 6 months after gene transfer, a polyclonal antibody against neurofibrillary tangles labeled cell bodies in a pattern similar to the tau immunoreactivity. 6 months after gene transfer, a monoclonal antibody against paired helical filament tau labeled apparent neuritic tauopathy in the basal forebrain. This antibody recognizes the epitope containing phosphorylated serine 212 and phosphorylated threonine.
Figure 3F:
Figure 4:
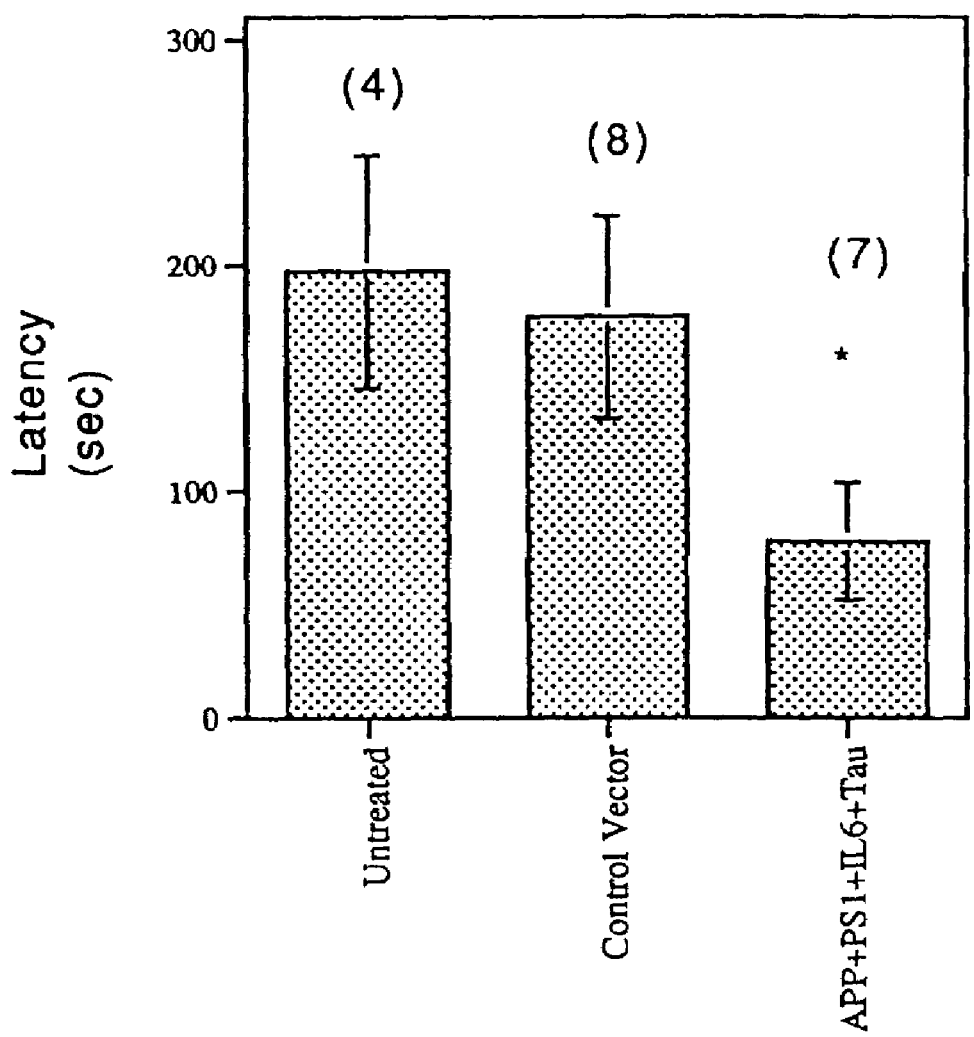
FIG. 4. Human α-synuclein gene transfer. (A) The control GFP-only vector produced robust expression of the marker gene GFP in neurons in the substantia nigra (native fluorescence of GFP). (B) The human A30P mutant α-synuclein-vector produced robust expression of α-synuclein immunoreactivity (stained with red) in the same area as (A) above. Nuclear counterstaining in blue. (C) Higher magnification shows accumulation of mutant α-synuclein in substantia nigra neuron cell bodies (similar staining method as in B). (C) Inset, α-synuclein immunoreactivity in a substantia nigra neuron visualized with a peroxidase staining method. (D–F) The morphology of axons of substantia nigra neurons that project to the striatum was altered by α-synuclein gene transfer. GFP labeling of α-synuclein vector-transduced fibers was dystrophic and included aberrant varicosities as shown by GFP native fluorescence, (D), and peroxidase labeling of GFP (E). In contrast, control-vector transduced Nigrostriatal axons labeled for GFP (as in E) were of uniform thickness. (A–F) Shows two-months post-injection of AAV vectors. Immunoreactivity for α-synuclein in neuronal cell bodies was never observed in control vector transduced or non-transduced tissues. The model therefore includes aberrant buildup of α-synuclein in substantia nigra neuron cell bodies, a hallmark feature of Parkinson's disease. Further, the induction of dystrophic nigrosrtiatal axons appears to mimic the Lewy neuritis found in Parkon's disease tissue as well as in many other forms of deurodegeneration and dementias.

FIGS. 3 and 4 hereof show similar types of aberrant gene expression for tau and synuclein, respectively. In each case, a similar procedure was used: a single injection of a vector was used to introduce the relevant gene into an appropriate brain region, followed by monitoring over sufficient intervals of up to several years for the relevant pathological morphology to develop.

In FIG. 3, plates B, C, and D are shown wherein tau protein aggregation induced by SGT of tau is demonstrated. In plate C, two months after injection of the human 4R P301L tau vector ($1\times10^9$ particles), tau immunoreactivity was found in cell bodies localized to the injection site in the medial septal/diagonal band area. The right side of the panel shows the non-transduced, surrounding tissue. In plate D, higher magnification of rat septal neurons expressing vector-derived human tau is shown. Some of the transduced neurons, like that shown in the inset, showed densely stained tau in the flame-like shape of neurofibrillary tangles. In plates A and B, co-localization of tau (stained with Texas red) and GFP (native fluorescence) is shown. This vector produces both tau and GFP bicistronically. While GFP filled the neurons and the nucleus, tau intensely accumulated in cell bodies, but not the nucleus. The filter set captured both red (tau) and green (GFP) fluorescence. This figure demonstrates that somatic gene transfer can increase tau expression and damage neurons in a manner seen in a variety of neurological disorders which encompass pathological deposits of tau, such as Alzheimer's disease, fronto-temporal dementia with Parkinsonism linked to chromosome 17, amyotropic lateral sclerosis, Down's syndrome, Hallervorden-Spatz disease, Jakob-Creutzfeldt disease, multiple system atrophy, Pick's disease, and others.

Furthermore, FIGS. 3E–3K show the expression of P301L tau, and that expression resulted in tau aggregation in neuronal cell bodies and dendrites of the adult rat basal forebrain. (E, F) Confocal imaging of fluorescently labeled tau (red) and bicistronic GFP native fluorescence, 2 months after tau vector gene transfer into the septum. Tau expression was somatodendritic as well as axonal, and punctate in places. At 6 months after gene transfer, a polyclonal antibody against neurofibrillary tangles labelled cell bodies in a pattern similar to the tau immunoreactivity. At 6 months after gene transfer, a monoclonal antibody against paired helical filament tau labeled apparent neuritic tauopathy in the basal forebrain. This antibody recognizes the epitope containing phosphorylated serine 212 and phosphorylated threonine.

FIG. 4. Human α-synuclein gene transfer. (A) The control GFP-only vector produced robust expression of the marker gene GFP in neurons in the substantia nigra (native fluorescence of GFP). (B) The human A30P mutant α-synuclein-vector produced robust expression of α-synuclein immunoreactivity (stained with red) in the same area as (A) above. Nuclear counterstaining in blue. (C) Higher magnification shows accumulation of mutant α-synuclein in substantia nigra neuron cell bodies (similar staining method as in B). (C) Inset, α-synuclein immunoreactivity in a substantia nigra neuron visualized with a peroxidase staining method. (D–F) The morphology of axons of substantia nigra neurons that project to the striatum was altered by α-synuclein gene transfer. GFP labeling of α-synuclein vector-transduced fibers was dystrophic and included aberrant varicosities as shown by GFP native fluorescence, (D), and peroxidase labeling of GFP (E). In contrast, control-vector transduced Nigrostriatal axons labeled for GFP (as in E) were of uniform thickness. (A–F) Shows two-months post-injection of AAV vectors. Immunoreactivity for α-synuclein in neuronal cell bodies was never observed in control vector transduced or non-transduced tissues. The model therefore includes aberrant buildup of α-synuclein in substantia nigra neuron cell bodies, a hallmark feature of Parkinson's disease. Further, the induction of dystrophic nigrosrtiatal axons appears to mimic the Lewy neuritis found in Parkon's disease tissue as well as in many other forms of deurodegeneration and dementias.

Accordingly, these data demonstrate successful induction of human neurodegenerative disease relevant morphology. Transfer of multiple genes according to this methodology results in variations and combinations of the results seen in these figures.

EXAMPLE 7

Figure 5A:
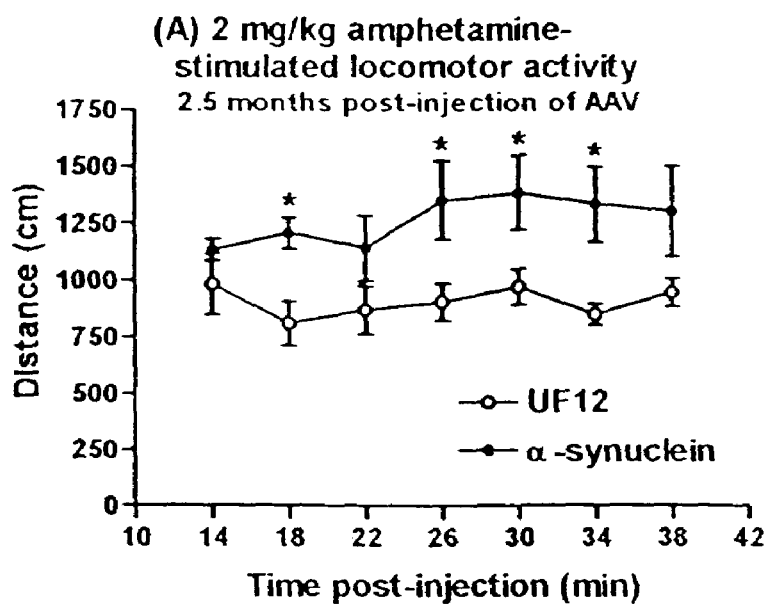
FIG. 5 shows data from groups of untreated or vector-injected rats tested for passive avoidance behavior over a 24 hour interval, four months after the injection of the indicated vector constructs into the septum and hippocampus. Animals received a brief (0.5 seconds) small (0.8 mA) foot shock at time 0 immediately after entering a dark room (training interval); their latency to enter the room 24 hours later was indicative of memory (testing interval). No difference was observed in the training intervals, a measure of locomotor activity (not shown). App, amyloid precursor protein; PS1, presenilin 1; IL6, interleukin 6; and tau protein. Each value is the mean±SEM of the number of animals noted in parentheses. *$p<0.05$ compared to either control group (rank order test).
Figure 5B:
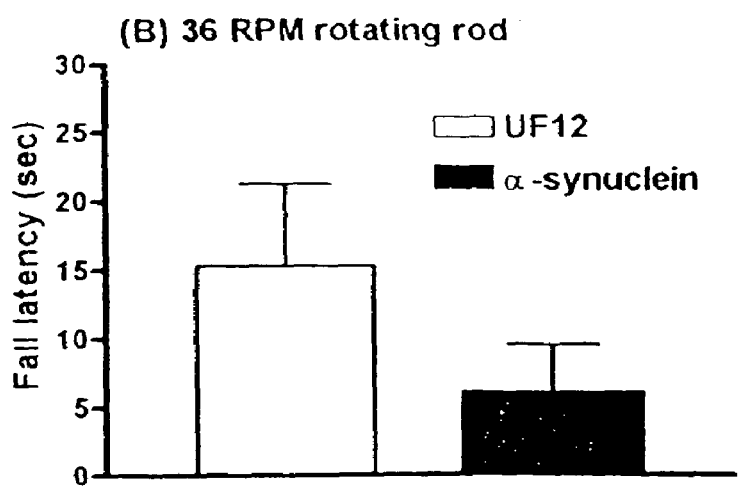

Behavioral Effects of Transferring Several Genes Related to Dementia into the Brain Adult male rats received intraseptal and intrahippocampal injections of a control AAV vector expressing GFP or a combination of vectors that encode amyloid precursor protein (APP), tau, IL6 and presenilin-1 (see FIG. 1). Expression of all genes (control and disease-related) was driven by the CBA promoter. Four months after injections, both groups were evaluated for memory related performance according to a passive avoidance paradigm, followed by an evaluation of their brains for gene expression. Another, untreated control group was included for determination of the potential toxic action of control AAV. The results shown in FIG. 5 show that there was a significant reduction in latency (memory of a mild foot shock 24 hours earlier) in the group of rats receiving the multiple dementia-related gene cocktail, compared to either of the other groups. The control vector had no effect on this memory related behavior.

Evaluation of brain tissues injected with the multiple vectors for the disease-related genes (APP+PS1+tau+IL6) revealed that multiple gene products were formed in the hippocampus. Typical pictures showing this multiple gene expression from the same injected brain, for example, are shown in FIG. 3. FIG. 2, top panel, shows neurons that are expressing transgenic APP, while the bottom panel shows neurons expressing transgenic PS-1 in the same brain region. FIG. 3A and 3B show the expression of transgenic tau (in association with APP, PS1 and IL6) in this region, with filamentous structures characteristic of this protein in neurons. Examples were found of an extracellular tau-immunoreactive deposit, about the size of a neuronal soma, in the toroidal shape reminiscent of the "ghost tangle" of Alzheimer's disease. These structures are believed to form when neurons with neurofibrillary tangles encircling the nucleus die; after all of the debris is removed, the insoluble tangle leaves a ring. A zone of reactive astrocytosis was observed around the injection site in the region containing GFP+neurons. No colocalization of GFP and GFAP (marker for glial cells, not neurons) was observed, although adjacent GFP+neurons and immunolabelled astrocytes were common, indicating that this vector delivery system was selective for neurons. These observations are consistent with a pathological effect of the polygenic transfection, such as that observed in a variety of neuropathological conditions.

EXAMPLE 8

Figure 6:
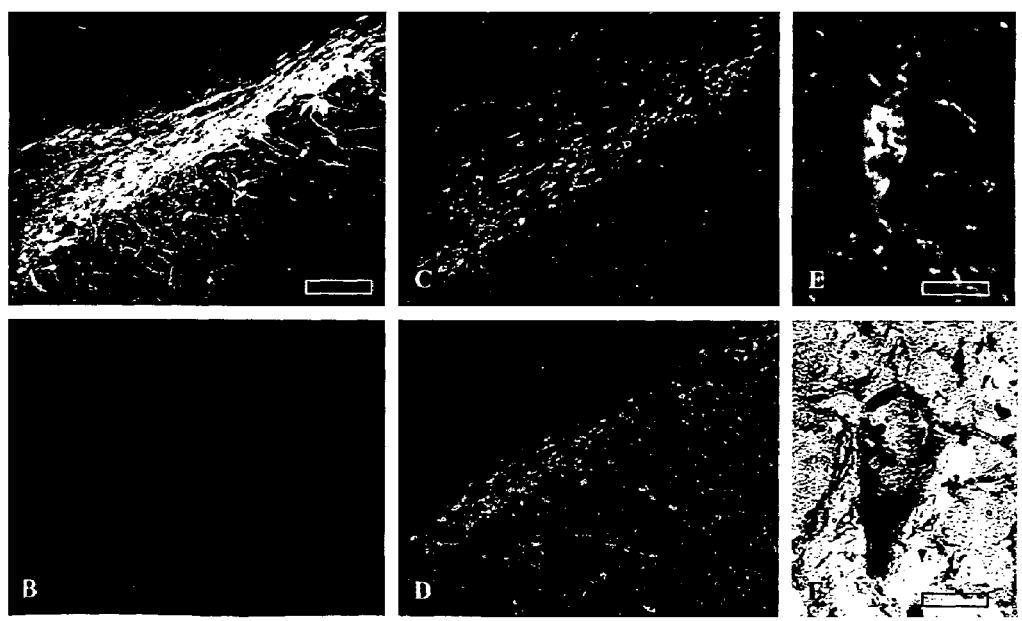
FIG. 6A shows amphetamine stimulated locomotor activity of animals that received either the GFP control vector (UF12) or the human A30P alpha-syn vector unilaterally in the substantia nigra. At 3 months after injection of a fixed dose of AAV ($1\times10^{10}$ particles), and 20 minutes following a 2 mg/kg administration of amphetamine challenge, alpha-syn animals were found to be 40% more active (total distance traveled in cm) over the 28 minute sessions. Two-way repeated measures ANOVA showed a main effect of the vector group ($F[1,10]=6.52$, $P=0.029$) and no effect of trial interval and no significant interaction. Post-hoc tests (Scheffe and Bonferonni/Dunn) showed significant group differences, $P<0.01$ for each test; n=6/group. Group differences in the means during the $2^{nd}$, $4^{th}$, $5^{th}$, $6^{th}$, trial intervals; *$P,0.05$, t-test. This figure demonstrates that the cellular effects of somatic gene transfer on synuclein expression are manifested by behavioral changes (locomotor activity) consistent with neurological damage—in this case, increased distance traveled during normal sleeping hours for the rat (roaming phenomenon). Eight months after transfer of alpha-synuclein for motor coordination on a rotating rod.
FIG. 6B, these animals were deficient in this activity measure, similar to other animal models for Parkinson's disease that are not genetic in nature. Testing rat motor coordination on a rotating rod is shown in FIG. 6B. The graph shows mean±SEM times for subjects (n=5–6/group) to fall off the rotating rod set at a speed of 36 RPM. The animals received either control vector or A30P alpha-synuclein vector eight months prior in the substantia nigra brain region. The Alpha-synuclein group fell of the rotating rod in 2.5-fold shorter times compared to the control vector group. These data demonstrate that overexpressing a mutant form of alpha-synuclein linked to Parkinson's disease induces behaviors characteristic of Parkinson's disease, i.e. impaired motor function.

Behavioral Effects of Transferring Alpha-Synuclein on Locomotor Activity and Cellular Morphology The alpha-synuclein gene has been associated with aberrant neuronal pathologies including Parkinson's disease. Using the AAV vector system, this gene was transduced into the substantia nigra of adult male rats, the brain region that degenerates in Parkinson's disease. Eight months later, they were assayed for motor coordination on a rotating rod (FIG. 6B). These animals were deficient in this activity measure, similar to other animal models for Parkinson's disease that are not genetic in nature. That this gene was expressed in the substantia nigra was demonstrated in FIG. 4H–J; neurons expressing this disease-related gene had punctate staining of their processes, similar to degenerating neurons in a variety of pathological conditions.

FIG. 6A shows amphetamine stimulated locomotor activity of animals that received either the GFP control vector (UF12) or the human A30P alpha-syn vector unilaterally in the substantia nigra. At 3 months after injection of a fixed dose of AAV ($1 \times 10^{10}$ particles), and 20 minutes following a 2 mg/kg administration of amphetamine challenge, alpha-syn animals were found to be 40% more active (total distance traveled in cm) over the 28 minute sessions. Two-way repeated measures ANOVA showed a main effect of the vector group (F[1,10]=6.52, P=0.029) and no effect of trial interval and no significant interaction. Post-hoc tests (Scheffe and Bonferonni/Dunn) showed significant group differences, P,0.01 for each test; n=6/group. Group differences in the means during the $2^{nd}$, $4^{th}$, $5^{th}$, $6^{th}$, trial intervals; *P,0.05, t-test. This figure demonstrates that the cellular effects of somatic gene transfer on synuclein expression are manifested by behavioral changes (locomotor activity) consistent with neurological damage—in this case, increased distance traveled during normal sleeping hours for the rat (roaming phenomenon).

Together, these results demonstrate that alpha-synuclein overexpression in a brain region associated with Parkinson's disease causes a behavioral deficit and cellular morphology typical of the disease. This study demonstrates the utility of this somatic transgene approach for modeling because more classic, much slower, mouse transgenic approaches are still attempting to demonstrate these phenomena.

What is claimed is:

1. A method for producing a model for neurofibrillary pathology which comprises somatically transferring a viral vector comprising a gene encoding an aberrant form of a human tau protein comprising the P301L mutation associated with fronto-temporal dementia with Parkinson's linked to chromosome 17 (FTDP-17) into brain tissue of a living rat or mouse under conditions which result in the expression of said gene; wherein expression of said gene results in a neurofibrillary pathology in said living rat or mouse comprising at least one characteristic selected from the group consisting of abnormal accumulation of tau in neuronal cell bodies and dendrites, presence of filaments immunoreactive for hyperphosphorylated tau, neuritic immunoreactivity with anti-neurofibrillary tangle antibody, and increase of reactive astrogliosis.

2. The method of claim 1, wherein said somatically transferring comprises injecting said viral vector into preselected areas of the brain of said living rat or mouse.

3. The method of claim 1, wherein said brain tissue comprises nigrastriatal neurons, septalhippocampal neurons, or both.

4. A method for inducing behavioral changes in a living rat or mouse which comprises somatically transferring an adeno-associated viral vector comprising a gene encoding an aberrant form of human tau protein comprising the P301L mutation associated with FTDP-17 directly into nigrastriatal neurons, septalhippocampal neurons, or both, in the brain of said living rat or mouse, wherein said somatically transferring said viral vector reduces memory in said living rat or mouse.

* * * * *

UNITED STATES PATENT AND TRADEMARK OFFICE
CERTIFICATE OF CORRECTION

PATENT NO. : 7,098,374 B2
APPLICATION NO. : 09/780041
DATED : August 29, 2006
INVENTOR(S) : Ronald Klein et al.

It is certified that error appears in the above-identified patent and that said Letters Patent is hereby corrected as shown below:

At Column 1, line 6, please delete "fights" and insert therefor --rights--.

Signed and Sealed this

Eleventh Day of December, 2007

JON W. DUDAS
*Director of the United States Patent and Trademark Office*